United States Patent
Kroll

(10) Patent No.: US 7,389,140 B1
(45) Date of Patent: Jun. 17, 2008

(54) ADJUSTMENT OF STIMULATION CURRENT PATH

(76) Inventor: Mark W. Kroll, 493 Sinaloa Rd., Simi Valley, CA (US) 93065

( * ) Notice: Subject to any disclaimer, the term of this patent is extended or adjusted under 35 U.S.C. 154(b) by 527 days.

(21) Appl. No.: 10/870,368

(22) Filed: Jun. 16, 2004

(51) Int. Cl.
A61N 1/36 (2006.01)
(52) U.S. Cl. .......................................... 607/9
(58) Field of Classification Search ............... 607/2, 607/4, 5, 9, 55, 56, 57, 74, 34
See application file for complete search history.

(56) References Cited

U.S. PATENT DOCUMENTS

| | | | | |
|---|---|---|---|---|
| 3,707,974 A | * | 1/1973 | Raddi | 607/27 |
| 3,835,865 A | * | 9/1974 | Bowers | 607/13 |
| 4,539,993 A | * | 9/1985 | Stanton | 607/43 |
| 4,558,702 A | * | 12/1985 | Barreras et al. | 607/30 |
| 4,712,555 A | | 12/1987 | Thornander et al. | 128/419 PG |
| 4,788,980 A | | 12/1988 | Mann et al. | 128/419 PG |
| 4,940,052 A | | 7/1990 | Mann et al. | 128/419 PG |
| 4,944,298 A | | 7/1990 | Sholder | 128/419 PG |
| 5,030,236 A | * | 7/1991 | Dean | 623/23.49 |
| 5,350,407 A | * | 9/1994 | McClure et al. | 607/16 |
| 5,411,547 A | * | 5/1995 | Causey, III | 607/129 |
| 5,439,760 A | * | 8/1995 | Howard et al. | 429/94 |
| 5,466,254 A | * | 11/1995 | Helland | 607/123 |
| 5,476,483 A | | 12/1995 | Bornzin et al. | 607/17 |
| 5,735,880 A | * | 4/1998 | Prutchi et al. | 607/9 |
| 5,895,733 A | * | 4/1999 | Crespi et al. | 429/219 |
| 6,141,585 A | * | 10/2000 | Prutchi et al. | 607/8 |
| 6,314,323 B1 | | 11/2001 | Ekwall | 607/23 |
| 6,363,288 B1 | * | 3/2002 | Bush et al. | 607/122 |
| 6,421,564 B1 | | 7/2002 | Yerich et al. | 607/9 |
| 6,477,037 B1 | * | 11/2002 | Nielsen et al. | 361/520 |
| 6,549,807 B1 | * | 4/2003 | Kroll | 607/34 |
| 6,591,133 B1 | * | 7/2003 | Joshi | 604/21 |
| 2002/0082651 A1 | * | 6/2002 | Stahmann et al. | 607/9 |
| 2002/0156512 A1 | * | 10/2002 | Borkan | 607/117 |
| 2004/0122490 A1 | * | 6/2004 | Reinke et al. | 607/60 |
| 2005/0090756 A1 | * | 4/2005 | Wolf et al. | 600/546 |
| 2005/0273170 A1 | * | 12/2005 | Navarro et al. | 623/17.13 |

FOREIGN PATENT DOCUMENTS

WO   WO 01/08748 A1   2/2001
WO   WO 01/36040 A1   5/2001

* cited by examiner

Primary Examiner—Carl H. Layno
Assistant Examiner—Jon-Eric Morales

(57) ABSTRACT

An exemplary implantable stimulation device includes an anode, a cathode, a circuit to generate an electrical potential between the anode and the cathode, and a resistance selected to divide current between a first current path to the anode and a second current path to the anode upon generation of the electrical potential between the anode and the cathode. Other exemplary methods, devices, systems, etc., are also disclosed.

30 Claims, 12 Drawing Sheets

EXEMPLARY CONFIGURATIONS
400

EXEMPLARY CIRCUITS
500

RESISTOR
510

ADJUSTABLE RESISTOR
514

DIODES AND
RESISTOR
520

DIODES AND
ADJUSTABLE RESISTOR
524

EXEMPLARY ADJUSTABLE RESISTOR CIRCUITS
600

EXEMPLARY
ADJUSTABLE RESISTOR
514

EXEMPLARY DIGITALLY PROGRAMMABLE
ADJUSTABLE RESISTOR
610

EXEMPLARY GATE SCHEMATIC
FOR AN ADJUSTABLE RESISTOR
620

EXEMPLARY GATE CONTROL FOR
AN ADJUSTABLE RESISTOR
630

EXEMPLARY METHOD

EXEMPLARY METHOD

ADJUSTMENT OF STIMULATION CURRENT PATH

TECHNICAL FIELD

Exemplary mechanisms presented herein generally relate to cardiac pacing, cardiac shock, sensing and/or stimulation therapies. Various exemplary mechanisms concern adjustment of current paths in a body.

BACKGROUND

Implantable cardiac stimulation devices generally include pacing devices, implantable cardiac defibrillation devices and devices that can delivery pacing and defibrillation therapy as appropriate. In general, activation of cardiac tissue occurs in response to current passing through myocardial tissue which causes the tissue to depolarize and contract. Conventional stimulation devices rely on electrode placement and/or selection of an electrode configuration to direct one or more current paths. Choice of electrode configuration is, of course, intimately tied to features of a stimulation device. For example, some conventional stimulation devices include a right ventricular lead only while others include a right ventricular lead and a left ventricular lead yet others may include only a general cardiac lead, a left ventricular lead, etc. While bi-ventricular pacing may be achieved using a variety of devices depending on device specifics, conventional bi-ventricular pacing is usually associated with stimulation devices that include at least one right ventricular lead and at least one left ventricular lead.

Conventional bi-ventricular devices typically achieve right ventricular activation without parasitic or inadvertent stimulation of the left ventricle; however, activation of the left ventricle without parasitic or inadvertent stimulation of the right ventricle has proven more problematic. Further, some individuals experience pain or "pocket stimulation" when too high of a current flows through the case of an implanted device. Of course, such pain or pocket stimulation may be avoided where a selected electrode configuration does not include using the case of the stimulation device as an electrode. Conventional approaches to these issues typically rely on judicious selection of electrode configuration. While selection of a particular electrode configuration may act to minimize or avoid parasitic stimulation, pocket stimulation, etc., such a selection may introduce limits that prevent delivery of an optimum therapy.

Various exemplary mechanisms are disclosed herein which aim to overcome at least some limitations associated with conventional cardiac stimulation devices. In particular, various exemplary mechanisms aim to minimize and/or avoid parasitic stimulation and/or patient pain.

SUMMARY

An exemplary implantable stimulation device includes an anode, a cathode, a circuit to generate an electrical potential between the anode and the cathode, and a resistance selected to divide current between a first current path to the anode and a second current path to the anode upon generation of the electrical potential between the anode and the cathode. Other exemplary methods, devices and/or systems are also disclosed.

In general, the various devices, systems and/or methods described herein, and equivalents thereof, are optionally suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are intended to be implemented in connection with any stimulation device that is configured or configurable to stimulate nerves and/or stimulate and/or shock a patient's heart. Various techniques may be implemented in connection with any stimulation, sensing and/or other device that relies on implantation of at least two dissimilar metals (e.g., metals, alloys, etc.) in a body and/or in contact with conductive body tissue, fluid, etc.

Figure 1:
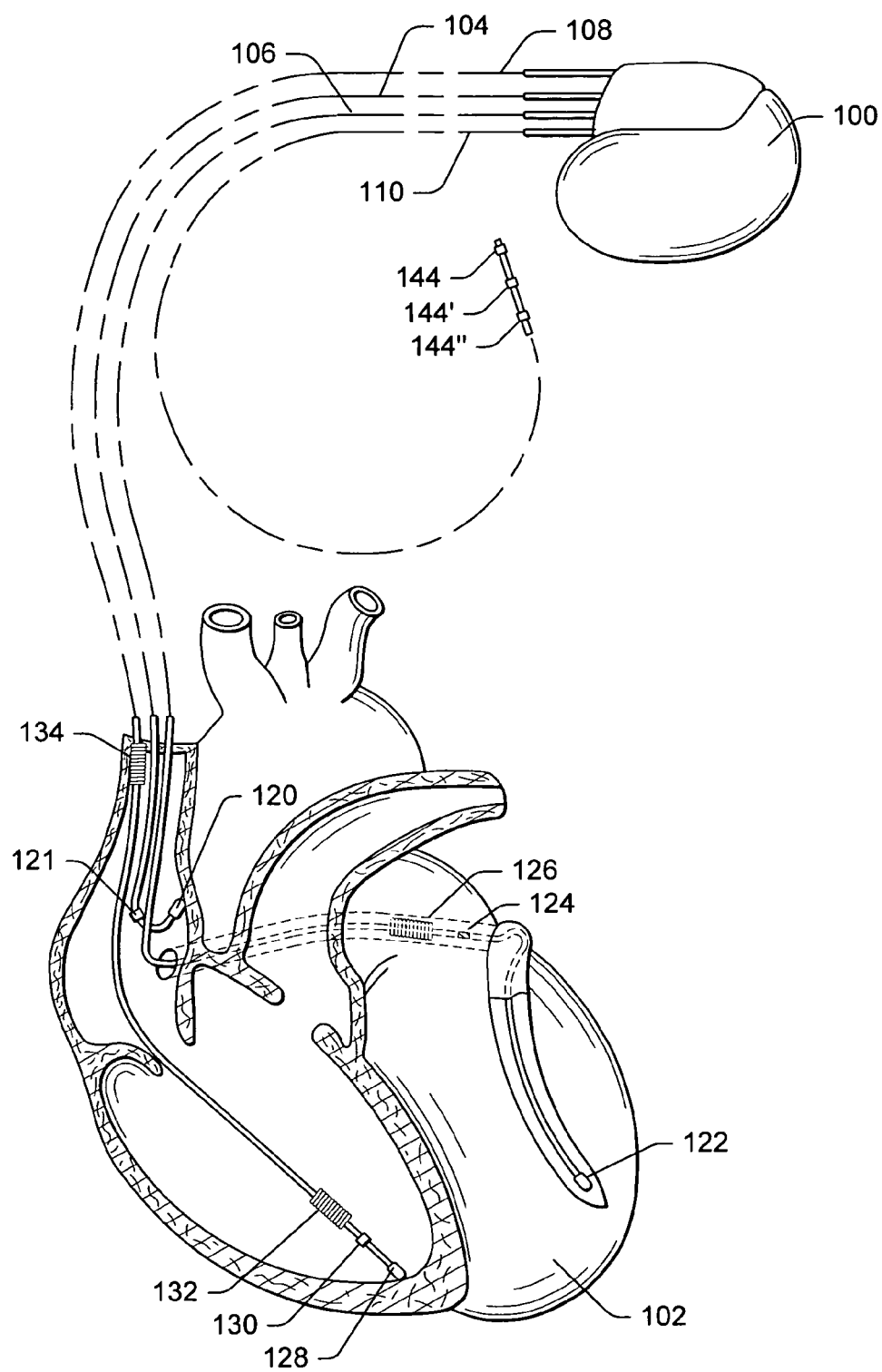
FIG. 1 is a simplified diagram illustrating an exemplary implantable stimulation device in electrical communication with at least three leads implanted into a patient's heart and at least one other lead for delivering stimulation and/or shock therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for stimulation of autonomic nerves, non-myocardial tissue, other nerves, etc. For example, this lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
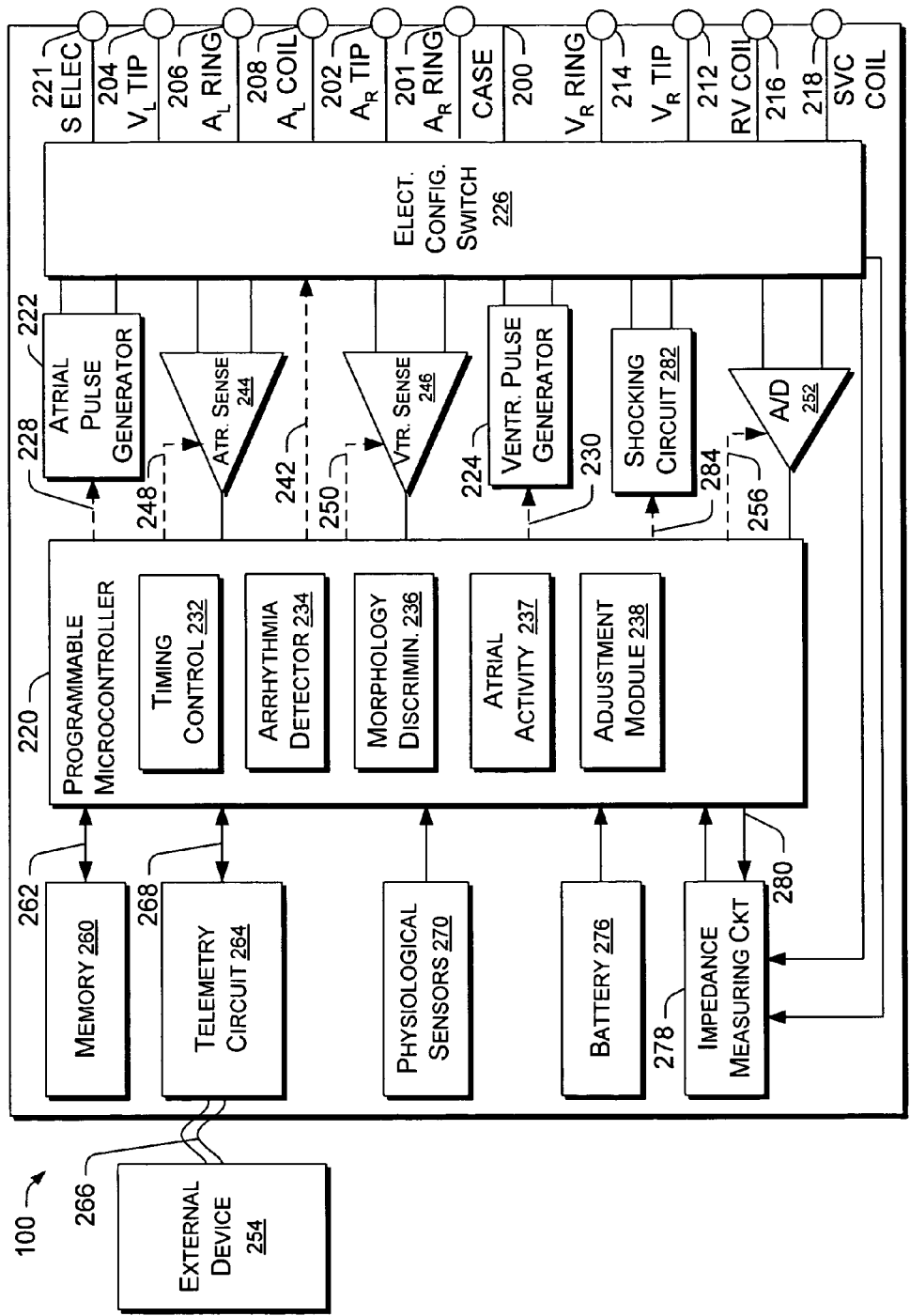
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an atrial activity analysis module 237. The atrial activity analysis module 237 optionally implements one or more methods for sensing, information analysis, and/or stimulation control related to atrial activity.

Microcontroller 220 further includes an adjustment module 238 for performing a variety of tasks related to, for example, adjustment of one or more resistances and/or selection of one or more electrode configurations. This component can be utilized by the stimulation device 100 in determining therapy in response to parasitic stimulation, pocket stimulation, pain, optimal current paths for stimulation, optimal current distribution amongst two or more current paths, etc. The adjustment module 238 may be implemented in hardware as part of the microcontroller 220, or as software/firmware instructions programmed into the device and executed on the microcontroller 220 during certain modes of operation. The adjustment module 238 may optionally implement various exemplary methods described herein.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the ICD device initiates defibrillation therapy.

While an ICD device may reserve defibrillation as a latter tier therapy, it may use defibrillation as a first-tier therapy for VF. In general, an ICD device does not synchronize defibrillation therapy with any given portion of a ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Figure 3:
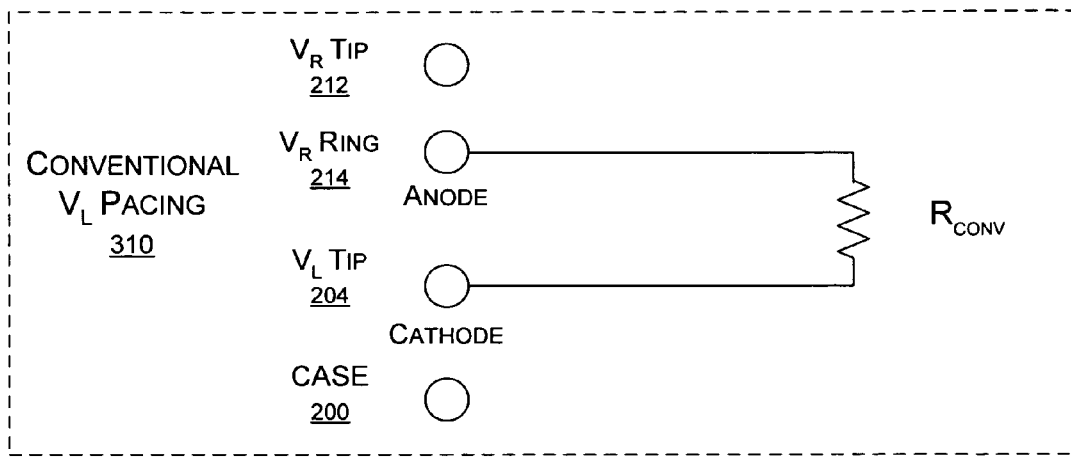
FIG. 3 is a diagram of various conventional pacing arrangements wherein a current path having a certain resistance exists in the body.
Figure 3:
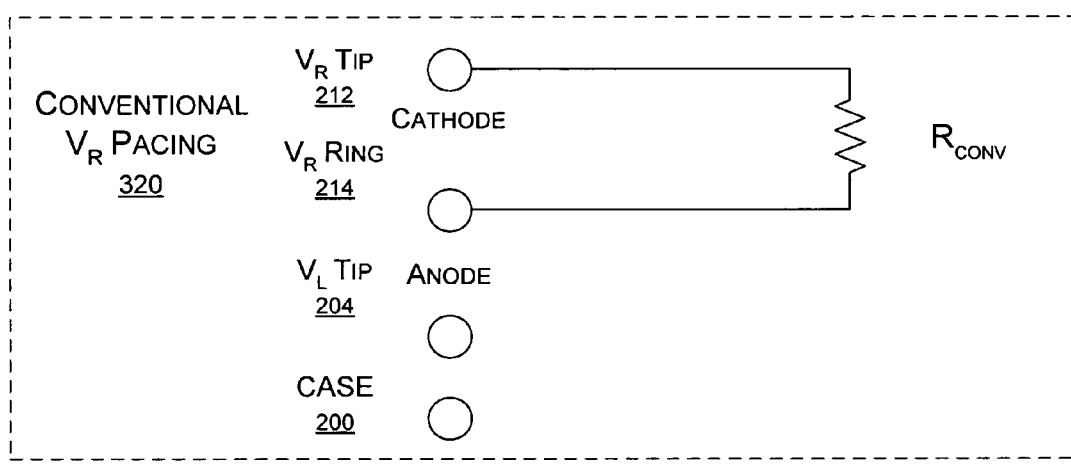
Figure 3:
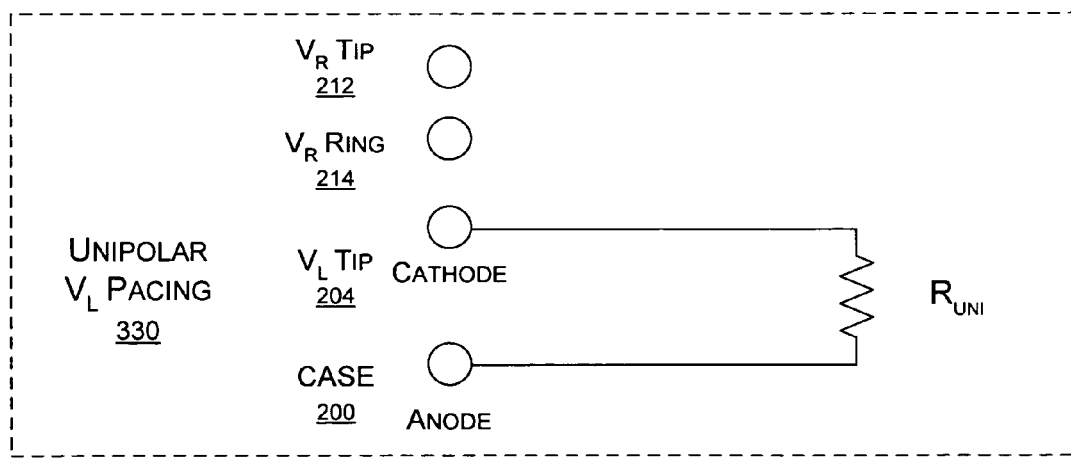

FIG. 3 shows various conventional electrode configurations associated with particular stimulation therapies 300. A conventional left ventricular pacing electrode configuration 310 includes use of a left ventricular tip electrode (e.g., to connector $V_L$ Tip 204) as a cathode and a right ventricular ring electrode as an anode (e.g., to connect $V_R$ Ring 214). Consequently, energy delivered by a pacing device will form a current path between the left ventricular tip electrode and the right ventricular ring electrode wherein current passes through tissue and/or fluid having a collective resistance of $R_{Conv}$. The inclusion of a right ventricular electrode in the current path can increase risk of parasitic stimulation of the right ventricle in response to delivery of a stimulation pulse for left ventricular stimulation.

A conventional right ventricular pacing electrode configuration 320 includes use of a right ventricular tip electrode (e.g., to connector $V_R$ Tip 212) as a cathode and a right ventricular ring electrode as an anode (e.g., to connect $V_R$ Ring 214). Consequently, energy delivered by a pacing device will form a current path between the right ventricular tip electrode and the right ventricular ring electrode wherein current passes through tissue and/or fluid having a collective resistance of $R_{Conv}$. This electrode configuration is often referred to as a bipolar configuration wherein the interelectrode spacing is relatively small compared to the spacing between an electrode and the case of the corresponding stimulation device.

A conventional unipolar left ventricular pacing electrode configuration 330 includes use of a left ventricular tip electrode (e.g., to connector $V_L$ Tip 204) as a cathode and a case electrode as an anode (e.g., to connect CASE 200). Consequently, energy delivered by a pacing device will form a current path between the left ventricular tip electrode and the case of the stimulation device wherein current passes through tissue and/or fluid having a collective resistance of $R_{Uni}$. This electrode configuration is often referred to as a unipolar configuration wherein interelectrode spacing is relatively large compared to spacing between two epicardial and/or chamber electrodes. This particular configuration has an associated risk of pocket stimulation and an increase in perceived pain due to currents flowing from the can into the sensitive pectoral region tissues and currents from the left ventricular tip stimulating the phrenic nerve thus sometimes causing an uncomfortable hiccup.

While the various conventional configurations refer to particular anodes and cathodes, other conventional configurations may use opposite electrode assignments. For example, in the unipolar left ventricular pacing configuration 330, the case of the implanted device may serve as a cathode and the left ventricular tip electrode may serve as an anode.

Figure 4:
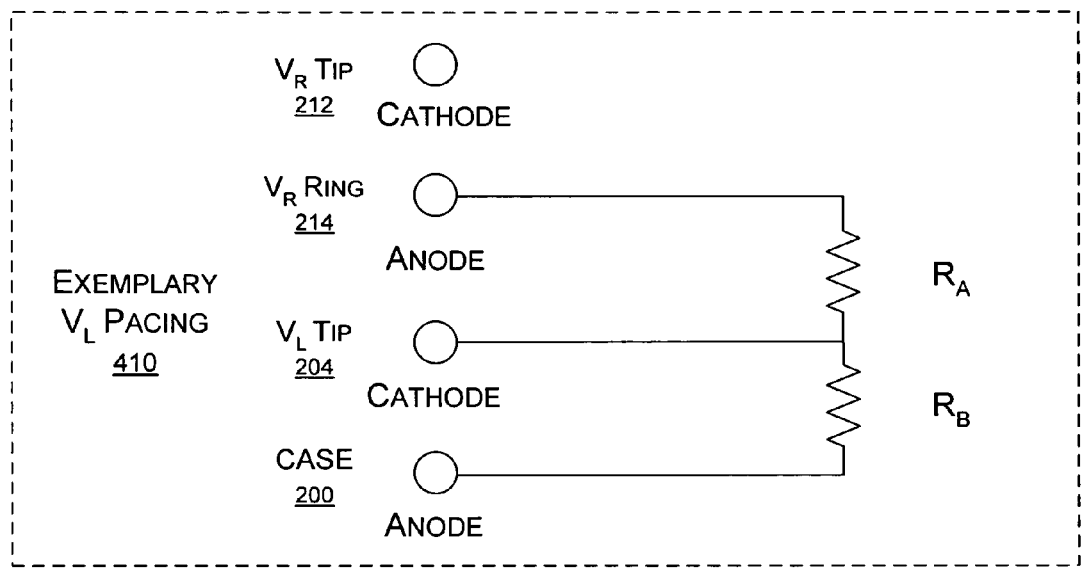
FIG. 4 is a diagram of various exemplary pacing arrangements wherein one or more current paths associated resistances exist in the body.
Figure 4:
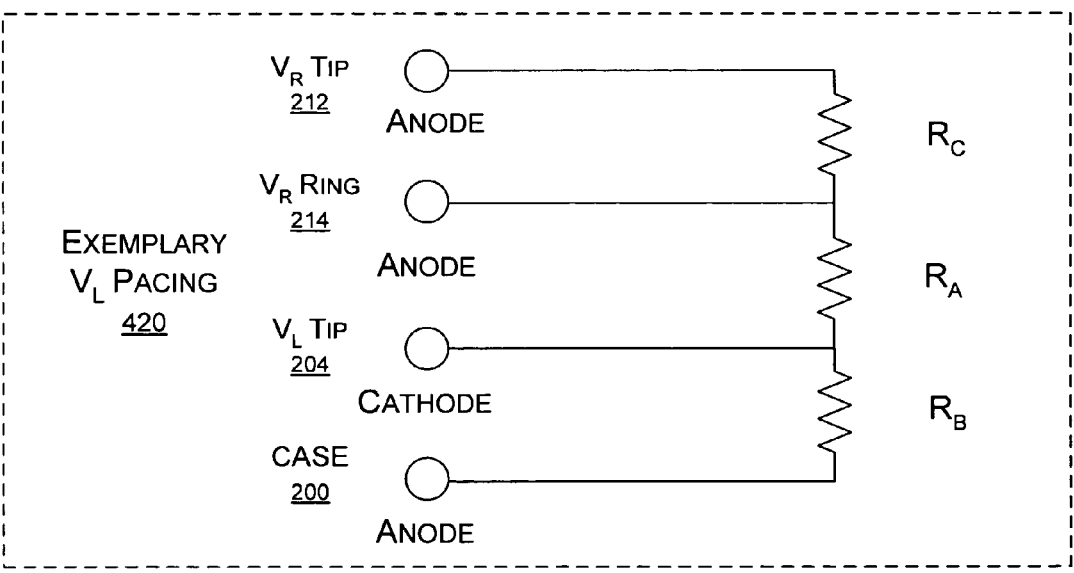

FIG. 4 shows various exemplary configurations for left ventricular pacing 400. The exemplary configurations 400 include more than one possible current path. For example, one exemplary configuration 410 includes use of a right ventricular ring electrode (e.g., the connector 214) as an anode, a case electrode (e.g., the connector 200) as an anode and a left ventricular tip electrode (e.g., the connector 204) as a cathode. Consequently, two current paths exist in the body as represented by resistances $R_A$ and $R_B$.

A second exemplary configuration 420 includes use of a right ventricular ring electrode (e.g., the connector 214) as an anode, a right ventricular tip electrode (e.g., the connector 212) as an anode, a case electrode (e.g., the connector 200) as an anode and a left ventricular tip electrode (e.g., the connector 204) as a cathode. Consequently, three current paths exist in the body as represented by resistances $R_A$, $R_B$ and $R_C$.

With respect to determining current in each path, the following equations (Eqns. 1-5) generally apply for circuits that include resistances in parallel. As applied in an in vivo scenario, such equations may be used to approximate resistance, voltage, current, etc., as in a bulk conductive medium, whether heterogeneous, homogeneous, etc., some "shared" resistance may exist. For example, a current path for a tip electrode may share a common path for at least part of a current path associated with another lead electrode in route to a case electrode. A third resistance may be used as appropriate to approximate or represent such a common resistance for two or more current paths.

$$R_{Total} = R_1 * R_2 / (R_1 + R_2) \quad (1)$$

$$V_{Total} = R_{Total} i_{Total} = i_{Total} * [R_1 * R_2 / (R_1 + R_2)] \quad (2)$$

$$i_{Total} = i_1 + i_2 \quad (3)$$

$$i_1 = V_{Total} / R_1 \text{ and } i_2 = V_{Total} / R_2 \quad (4)$$

$$i_1 = i_{Total} * [R_2 / (R_1 + R_2)] \text{ and } i_2 = i_{Total} * [R_1 / (R_1 + R_2)] \quad (5)$$

With respect to the exemplary configurations, Eqns. 1-5 may be used to determine current through each resistance.

In general, a stimulation device has no control over the amount of current directed across each resistance. As described herein, an exemplary mechanism allows for adjustment of current over two or more current paths either via a controller of an implanted device, an external controller, at the time of or prior to implantation of an implanted device, etc. The exemplary mechanism involves use of one or more resistances between a cathode and an anode to thereby limit current or to selectively divide current between a plurality of current paths.

Figure 5:
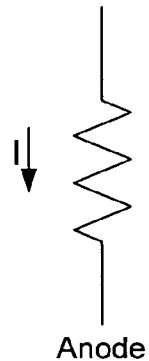
FIG. 5 is a schematic of various exemplary circuits for controlling current to one or more current paths.
Figure 5:
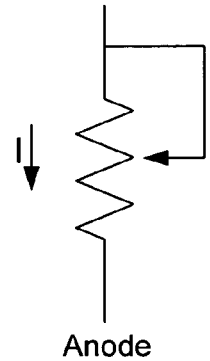
Figure 5:
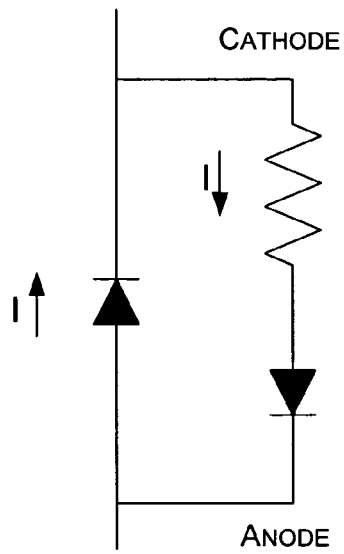
Figure 5:
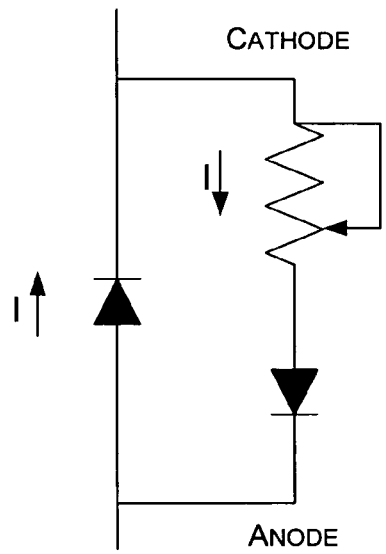

FIG. 5 shows various exemplary circuits 500 capable of selectively dividing current between a plurality of current paths. A first exemplary circuit 510 includes a resistor having a resistance between an anode and a cathode. Current across the resistor is in the direction of cathode to anode. Such a resistance is optionally inserted into an implantable stimulation device and/or a conductor of a lead to thereby affect current division amongst a plurality of current paths. The resistive value of the resistor 510 is optionally selected prior to implantation of a device or a lead.

A second exemplary circuit includes an adjustable resistor 514 positioned between an anode and a cathode. In this example, the adjustable resistor 514 may be a potentiometer that includes a high end, a low end and an adjustable wiper that has an electrical contact to the high end. Movement of the wiper thereby acts to adjust the resistance of the exemplary circuit 514 as it appears in a path between a cathode and an anode.

A third exemplary circuit includes a resistor and two diodes 520. The diodes act to limit current to a delivery path or a return path depending on direction of current. The return path includes a cathode, a resistor, a diode and an anode. The resistor limits current and the diode allows for current to flow from cathode to anode but not in the reverse direction. In general, the exemplary circuit 520 provides a unidirectional low resistance current path and a unidirectional high resistance path. Such a circuit is optionally suitable for use with electrodes that are used for more than one purpose, for example, sensing, pacing and/or shocking.

A fourth exemplary circuit includes an adjustable resistor and two diodes 524. The diodes act to limit current to a delivery path or a return path depending on direction of current. The return path includes a cathode, an adjustable resistor, a diode and an anode. The adjustable resistor limits current and the diode allows for current to flow from cathode to anode but not in the reverse direction. In general, the exemplary circuit 524 provides a unidirectional low resistance current path and a unidirectional adjustable and typically higher resistance path. Such a circuit is optionally suitable for use with electrodes that are used for more than one purpose, for example, sensing, pacing and/or shocking.

Figure 6:
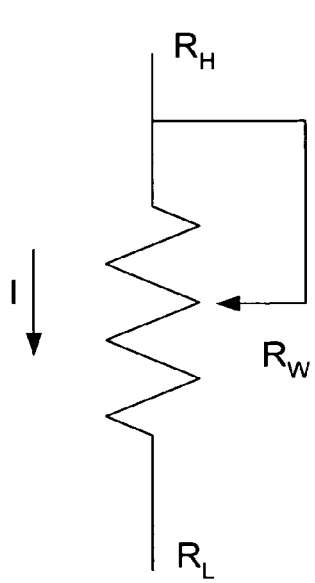
FIG. 6 is a schematic of various exemplary adjustable resistor circuits capable of controlling current to one or more current paths.
Figure 6:
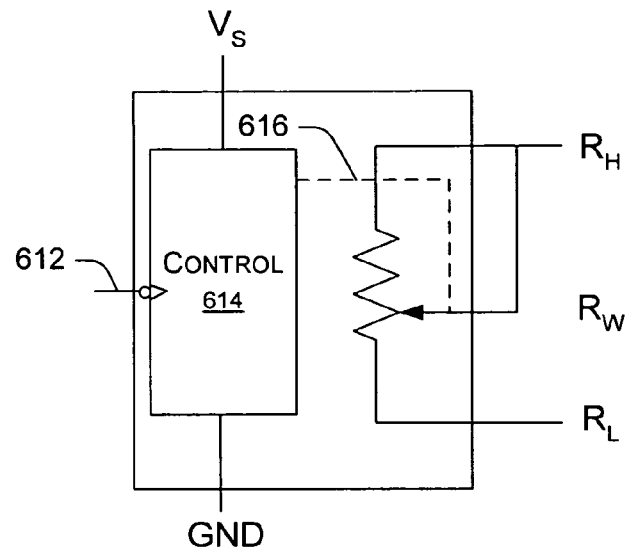
Figure 6:
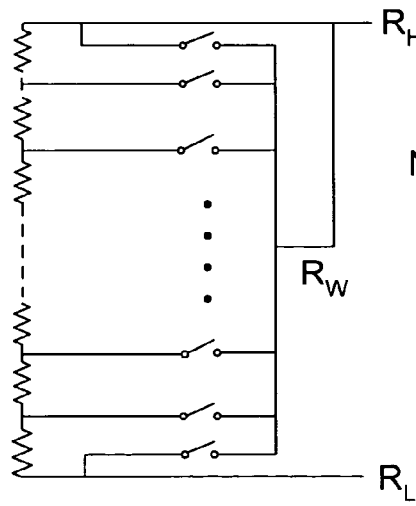
Figure 6:
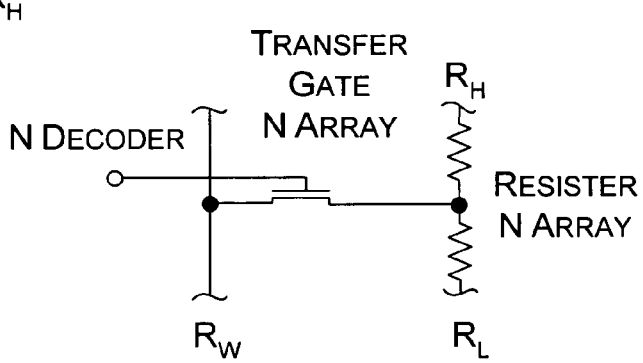

FIG. 6 shows various exemplary circuits that include adjustable resistors 600. A first circuit 514 is the same as the circuit 514 of FIG. 5 and includes labels for a high end ($R_H$), a low end ($R_L$) and a wiper ($R_W$). A second circuit includes a digitally programmable adjustable resistor 610 (e.g., DPAR). The DPAR 610 includes an input for input to a digital controller 614, which is powered by a supply voltage $V_S$. The controller 614 includes a control line (dashed line) that can adjust the wiper ($R_W$) of a variable resistor and thus adjust the resistance between the high end ($R_H$) and the low end ($R_L$). Such digitally programmable adjustable resistors are commercially available, for example, from Catalyst Semiconductor, Inc. (Sunnyvale, Calif.) and others.

A third circuit includes a gate schematic for an adjustable resistor 620. The schematic includes a series of resistors and a series of gates wherein the state of any particular gate can affect the overall resistance between $R_H$ and $R_L$. A fourth circuit includes a gate control suitable for use with the circuits 610, 620. The circuits 610, 620 may include a plurality of such gate controls depending on requirements, etc. In general, a decoder (e.g., n bit) acts to control an array of gates (e.g., n gates) which in turn controls resistance with respect to a resistor array (e.g., n resistors).

Figure 7:
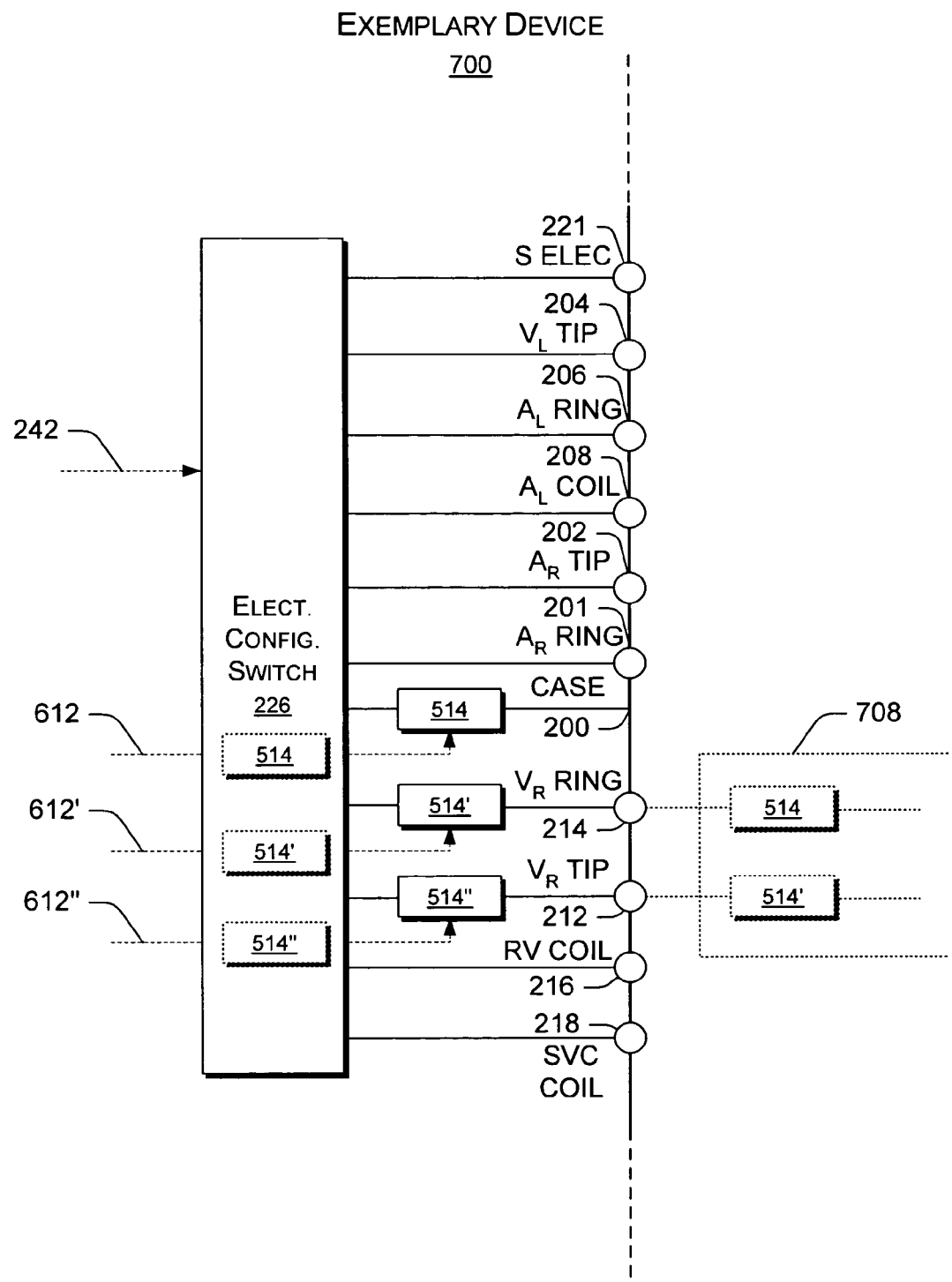
FIG. 7 is a diagram that includes one or more exemplary circuits to control current to one or more current paths.

FIG. 7 shows an exemplary device 700 that includes various features of the device 100 of FIGS. 1 and 2. In this example, the device 700 includes one or more adjustable resistors 514, 514', 514". The one or more adjustable resistors 514, 514', 514" are optionally positioned between a connector 200, 212, 214 (or other connectors) and a multiplexer switch 226, integrated in the multiplexer switch 226 (shown as dashed boxes), between the multiplexer switch 226 and other circuitry (not shown), and/or between a conductor of a lead 708 and the electrode of the lead 708 (shown as dashed boxes). The exemplary device 700 includes control lines 612, 612', 612" for the adjustable resistors 514, 514', 514" as positioned between the electrical configuration switch 226 and the connectors 200, 212, 214. In an alternative example, where the switch 226 includes integral adjustable resistors, the control line 242 optionally allows for control of resistance.

Figure 8:
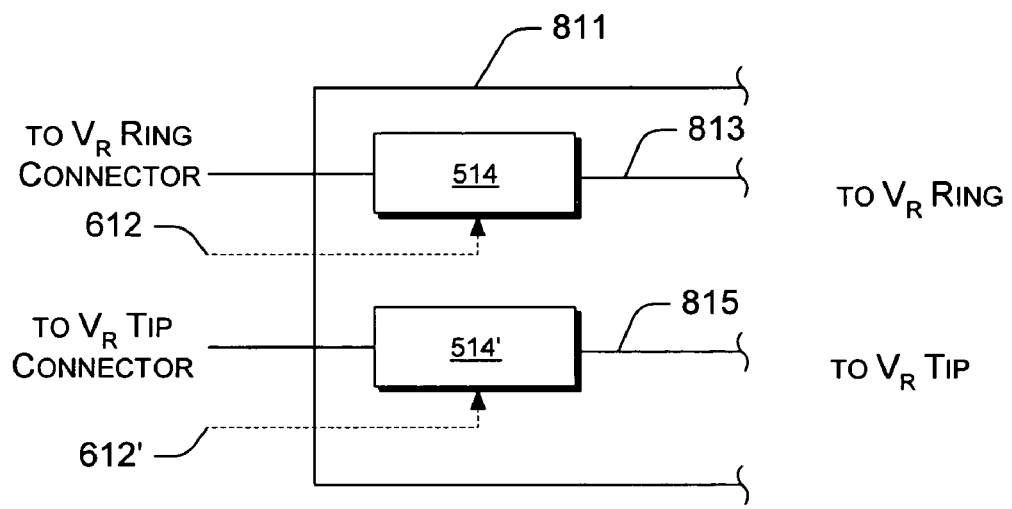
FIG. 8 is a diagram of a portion of an exemplary lead that includes one or more circuits to control current to one or more current paths.

FIG. 8 shows an exemplary lead 808 that includes a lead body 811 and lead conductors 813, 815. The lead conductor 813 connects to a right ventricular ring electrode and also allows for connection to a right ventricular ring connector of an implantable device. An adjustable resistor 514 is disposed between the electrode and the point of contact for connection to the connector of an implantable device. In this example, a control line 612 allows for adjustment of resistance of the resistor 514. The control line 612 may connect to an implantable device via an appropriate control line connector. In another example, a lead conductor serves to connect to an electrode, to a connector of an implantable device and to receive a control signal to adjust resistance of an adjustable resistor. In this latter example, a signal is typically transmitted from an implantable device to the adjustable resistor in a manner that does not interfere with operation of an electrode in electrical contact with the lead conductor. The other lead conductor 815 connects to a right ventricular tip electrode and also allows for connection to a right ventricular tip connector of an implantable device. An adjustable resistor 514' is disposed between the electrode and the point of contact for connection to the connector of an implantable device. In this example, a control line 612' allows for adjustment of resistance of the resistor 514'. Control of the resistor 514' is optionally achieved by any of a variety of signal communication techniques, including those mentioned above.

Figure 9:
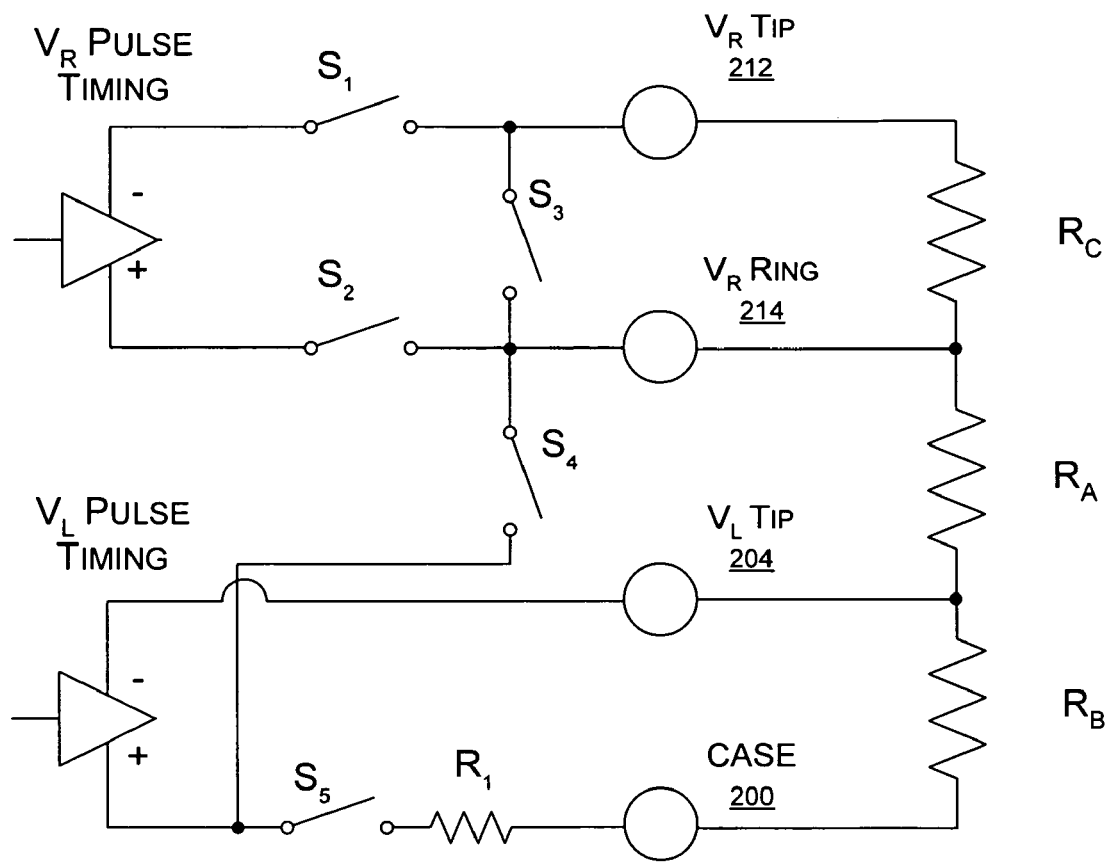
FIG. 9 is a schematic of an exemplary circuit capable of directing stimulation energy to one or more current paths.

FIG. 9 shows an exemplary circuit 900 suitable for controlling delivery times of stimulation pulses to various electrodes. The circuit includes a right ventricular pulse timing section and a left ventricular pulse timing section. The right ventricular pulse timing section includes a connector 212 to a right ventricular tip electrode conductor and to a connector 214 to a right ventricular ring electrode conductor. A resistance R ($V_R$) exists between the right ventricular tip and ring electrodes due to body tissue and/or fluid. The left ventricular pulse timing section includes a connector 204 to a left ventricular tip electrode and a connector 200 to a case electrode. Thus, as shown, the exemplary circuit allows for delivery of stimulation to the left ventricle using a unipolar electrode configuration.

The exemplary circuit 900 includes five switches $S_1$, $S_2$, $S_3$, $S_4$, $S_5$, which are controllable via appropriate connection to a microcontroller (e.g., the programmable microcontroller 220 of FIG. 2). The various switches allow for electrical connections between electrodes of the right ventricular section and the left ventricular section (see, e.g., exemplary electrode connections of FIG. 2). Further, the left ventricular section includes a resistor $R_1$ positioned between the switch $S_5$ and the case connector 200. This resistor is optionally selected to limit current or to divide current between a plurality of current paths, depending on electrode configuration, which may be selected on the basis of one or more of the switches $S_1$, $S_2$, $S_3$, $S_4$, $S_5$. For example, if $S_4$ and $S_5$ are "on", then return current for the LV tip electrode may split between two current paths.

Figure 10:
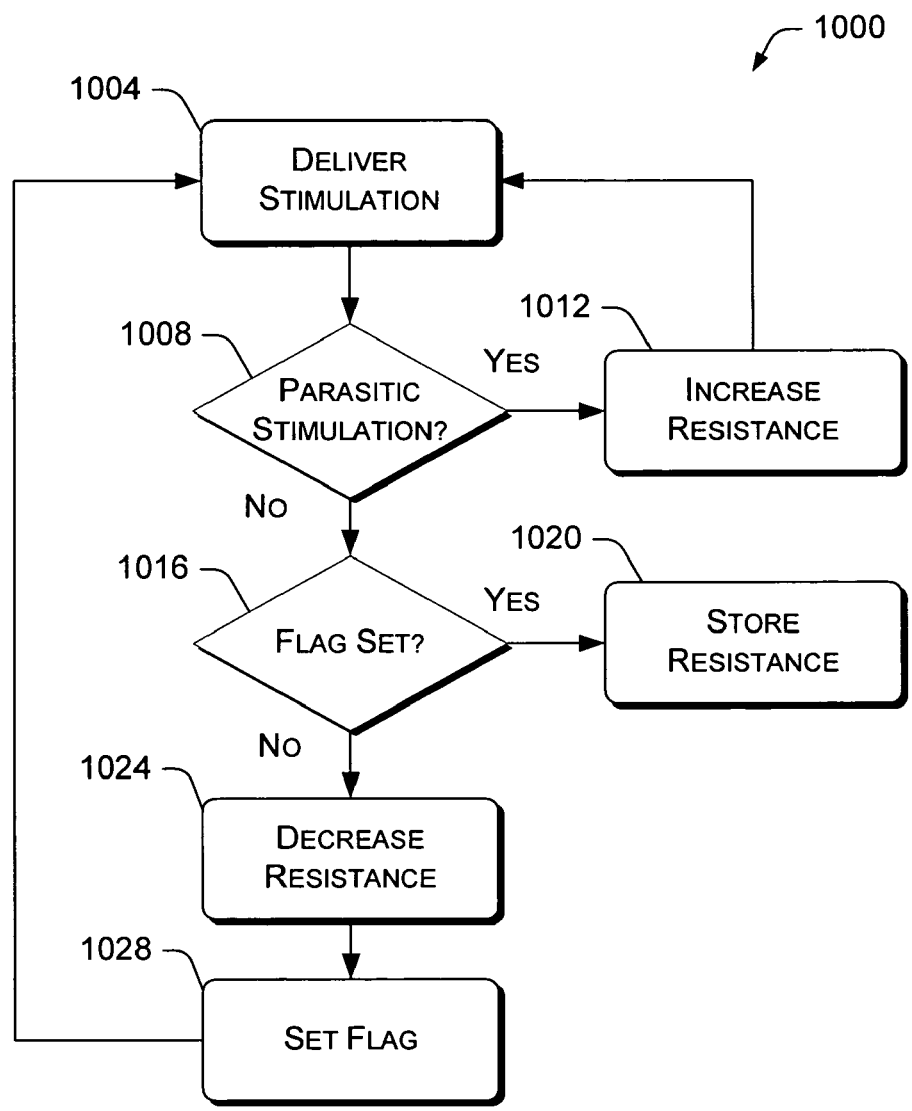
FIG. 10 is a block diagram of an exemplary method for adjustment of current to one or more paths to minimize or avoid parasitic stimulation.

FIG. 10 shows a block diagram of an exemplary method 1000 for adjustment of resistance in relation to parasitic or inadvertent stimulation. According to the method 1000, a delivery block 1004 calls for delivery of stimulation. A decision block 1008 follows that decides if the delivered stimulation caused any substantial parasitic stimulation. If the decision block 1008 decides that substantial parasitic stimulation occurred, then the method 1000 continues in an increase resistance block 1012, which acts to increase resistance of a current path associated with the parasitic stimulation. For example, if the parasitic stimulation was associated with an electrode in the right ventricle, then the resistance of an adjustable resistor would be increased to limit current through this resistor or to divide the total current differently between the various current paths. Of course, alternatively or additionally, a resistance may be decreased in another current path that has little risk of being associated with parasitic stimulation, which, in turn, would direct more current to the low risk path. The delivery block 1004 would follow the increase block 1012 wherein stimulation energy may remain essentially the same.

If the decision block 1008 decides that no substantial parasitic stimulation occurred (e.g., tolerable within some limit(s)), then a subsequent decision block 1016 follows that decides if a flag or other marker indicative of no prior decrease in resistance has been set. If such a flag has been set, then there may be little need for a further decrease in resistance as parasitic stimulation has been avoided. Consequently, a storage block 1020 follows wherein the resistance value is stored in a manner that associates the resistance value with no parasitic stimulation for the given conditions (e.g., electrode configuration, stimulation energy, duration, etc.). While not shown, the method 1000 may continue at the delivery block 1004 or at another therapy block as appropriate.

If the decision block 1016 decides that no flag or marker has been set, then the method 1000 continues in a decrease resistance block 1024. The decrease resistance block 1024 acts to decrease resistance in a current path associated with a risk of parasitic stimulation. Of course, alternatively or additionally, a resistance may be increased in another current path that has little risk of being associated with parasitic stimulation. A set block 1028 follows the decrease block 1024 which sets a flag or marker to indicate that a decrease in resistance has occurred over a current path associated with a risk of parasitic stimulation. The method 1000 then returns to the delivery block 1004. The detection of RV stimulation, phrenic nerve stimulation, or pectoral pain is optionally performed by physician questioning of a patient and/or through detection or observation of symptoms. Such detection or observation may be accomplished automatically. For example, the "anodal" RV capture may be readily detected by electrogram changes. Phrenic nerve stimulation may be detectable by changes in one or more chest dimension (e.g., measured by "minute ventilation" impedance monitoring, etc.). Pectoral stimulation is optionally measured by correlation of the pacing pulse to information acquired via an internal acceleration sensor (e.g., an accelerometer). Various exemplary methods, devices, systems, etc., optionally rely on such techniques, for example, to adjust one or more parameters associated with delivery of stimulation (e.g., pulse, shock, etc.).

Figure 11:
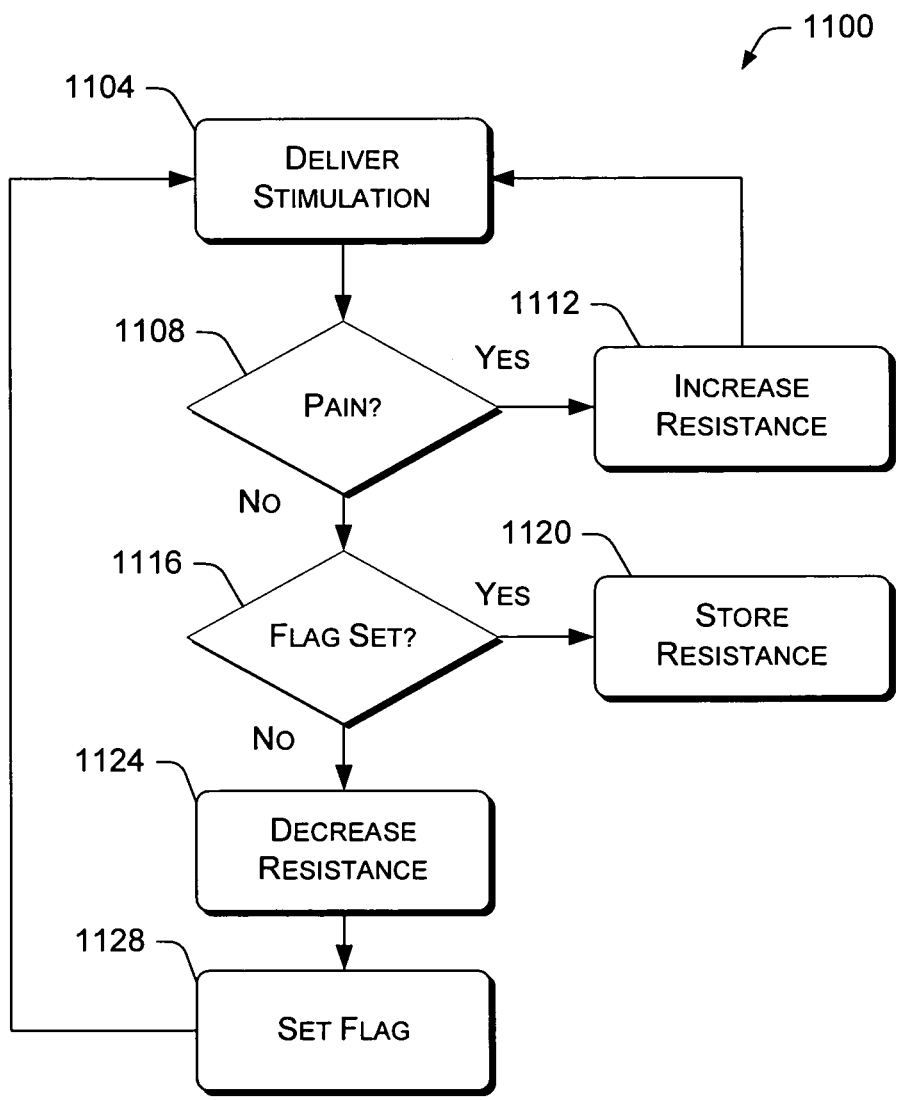
FIG. 11 is a block diagram of an exemplary method for adjustment of current to one or more paths to minimize or avoid pain or pocket stimulation.

FIG. 11 shows a block diagram of an exemplary method 1100 for adjustment of resistance in relation to pain or pocket stimulation associated with a case electrode. Thus, according to the method 1000, a delivery block 1104 calls for delivery of stimulation wherein at least one current path includes a case electrode of an implantable stimulation device. A decision block 1108 follows that decides if the delivered stimulation caused any substantial pain or pocket stimulation. If the decision block 1108 decides that substantial pain or pocket stimulation occurred, then the method 1100 continues in an increase resistance block 1112, which acts to increase resistance of a current path associated with the case electrode to limit current through this path or to divide the total current differently between the various current paths. Of course, alternatively or additionally, a resistance may be decreased in another current path that has little risk of being associated with pain or pocket stimulation, which, in turn, would direct more current to the low risk path. The delivery block 1104 would follow the increase block 1112 wherein stimulation energy may remain essentially the same.

If the decision block 1108 decides that no substantial pain or pocket stimulation occurred, then a subsequent decision block 1116 follows that decides if a flag or other marker indicative of no prior decrease in resistance has been set. If such a flag has been set, then there may be little need for a further decrease in resistance as pain or pocket stimulation has been avoided. Consequently, a storage block 1120 follows wherein the resistance value is stored in a manner that associates the resistance value with no substantial pain or pocket stimulation for the given conditions (e.g., electrode configuration, stimulation energy, duration, etc.). While not shown, the method 1100 may continue at the delivery block 1104 or at another therapy block as appropriate.

If the decision block 1116 decides that no flag or marker has been set, then the method 1100 continues in a decrease resistance block 1124. The decrease resistance block 1124 acts to decrease resistance in a current path associated with a risk of pain or pocket stimulation. Of course, alternatively or additionally, a resistance may be increased in another current path that has little risk of being associated with pain or pocket stimulation. A set block 1128 follows the decrease block 1124 which sets a flag or marker to indicate that a decrease in resistance has occurred over a current path associated with a risk of pain or pocket stimulation. The method 1100 then returns to the delivery block 1104.

While the exemplary methods 1000 and 1100 are shown and discussed separately, they are optionally combined in a manner that acts to achieve stimulation in a manner that minimizes parasitic stimulation, pain and/or pocket stimulation. In general, such a method acts to adjust one or more resistances that, in turn, alter current over two or more current paths. As described herein, such resistances may be achieved via variable or adjustable resistors including potentiometers and/or digitally programmable potentiometers. Such potentiometers are optionally positioned in or associated with an implantable device and/or positioned in or associated with a lead.

Various exemplary methods, devices and/or systems described herein optionally include directing stimulation energy (e.g., pacing, shock, etc.) across various current paths according to time. For example, a first phase of biphasic stimulation may be directed to primarily one current path and then a second phase of the stimulation directed to primarily another current path. Of course, such a mechanism may be applied to a monophasic pulse as well.

Figure 12:
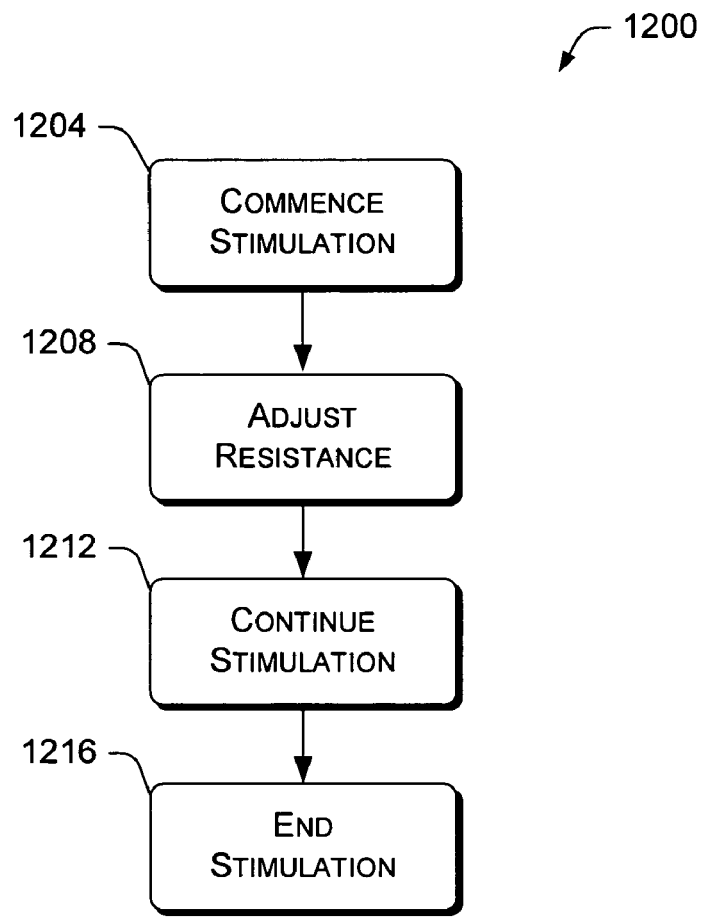
FIG. 12 is a block diagram of an exemplary method for adjusting resistance during delivery of stimulation energy.

FIG. 12 shows a block diagram of an exemplary method 1200 wherein an adjustment to resistance occurs between commencing stimulation and ending stimulation. In a commencement block 1204, stimulation commence as appropriate, for example, according to an electrode configuration that direct the current along one or more current paths. An adjustment block 1208 follows wherein an adjustment occurs to at least one resistance associated with the one or more current paths. In an alternative exemplary method, an adjustment occurs along with a change in electrode configuration. For example, an adjustment in electrode configuration may add another electrode to thereby provide for another current path. A continue block 1212 indicates that, in this example, delivery of stimulation energy may occur during the adjustment and/or immediately after the adjustment to resistance. For example, consider a biphasic pulse wherein a first phase is delivered using a first set of resistances and wherein a second phase is delivered using a second set of resistances. At sometime thereafter, an end block 1216 ends delivery of the stimulation energy. Such an exemplary method may rely on any particular features of the multiplexer 226, the microcontroller 220, circuitry of other various figures, etc. Such an exemplary method may be used in response to pain, parasitic stimulation, etc., wherein an adjustment of resistance and/or electrode configuration during delivery of stimulation energy acts to reduce pain and/or risk of parasitic stimulation. Accordingly, an exemplary method may call for commencement of delivery of stimulation energy using an electrode configuration and call for adjustment of at least one resistance associated with the electrode configuration during the delivery of the stimulation.

An exemplary implantable stimulation device may include an anode, a cathode, a circuit to generate an electrical potential between the anode and the cathode, and a circuit to adjust a resistance to divide current between a first current path to the anode and a second current path to the anode during generation of the electrical potential between the anode and the cathode. In this or another example, an exemplary implantable device includes a circuit to adjust a resistance to divide current between a first current path to the anode and a second current path to the anode after generation of the electrical potential between the anode and the cathode and prior to generation of another electrical potential. In such an example, the electrical potential and the other electrical potential are optionally generated using different electrode configurations, optionally different, optionally different in phase, etc. In such an exemplary device, the resistance is optionally provided by a digitally controllable potentiometer.

CONCLUSION

Although exemplary mechanisms have been described in language specific to structural features and/or methodological acts, it is to be understood that the subject matter defined in the appended claims is not necessarily limited to the specific features or acts described. Various exemplary methods or portions thereof are optionally implemented with respect to software, hardware, firmware, etc. Computer-readable media optionally store instructions pertaining to various exemplary methods or portions thereof.

What is claimed is:

1. An implantable stimulation device comprising:
   first and second anode electrodes adapted for placement in, on or near a heart;
   a cathode electrode adapted for placement in, on or near a heart;
   a battery separate from the first and second anode electrodes and the cathode electrode and having an anode terminal coupled to the first anode electrode and the second anode electrode and a cathode terminal coupled to the cathode electrode, the battery configured to generate an electrical potential between the first anode electrode and the cathode electrode and the second anode electrode and the cathode electrode; and
   a resistance device separate from the battery and coupled between one of the anode terminal and the first anode electrode, the anode terminal and the second anode electrode and the cathode terminal and the cathode electrode and having a resistance selected to divide current between a first current path between the first anode electrode and the cathode electrode and a second current path between the second anode electrode and the cathode electrode upon generation of the electrical potential.

2. The device of claim 1 wherein the resistance device comprises an adjustable resistor.

3. The device of claim 1 wherein the resistance device comprises a digitally controllable potentiometer.

4. The device of claim 1 further comprising a programmable controller capable of controlling the resistance.

5. The device of claim 4 wherein the programmable controller controls the resistance using a digitally programmable potentiometer.

6. The device of claim 1 wherein the resistance is selected to minimize risk of parasitic stimulation of myocardial tissue.

7. The device of claim 1 wherein the resistance is selected to minimize risk of pocket stimulation.

8. The device of claim 1 wherein one of the first anode electrode and the second anode electrode comprise a case.

9. The device of claim 8 wherein the resistance is selected to achieve an acceptable level of current to the case.

10. The device of claim 1 wherein one or more of the first anode electrode, the second anode electrode and the cathode electrode are associated with an implantable lead.

11. The device of claim 1 further comprising a bidirectional circuit coupled to the resistor that directs current from the electrode to the device along a path of first resistance and from the device to the electrode along a path of second resistance.

12. The device of claim 11 wherein the electrode-to-device path includes the resistance.

13. The device of claim 11 wherein the electrode-to-device path includes an adjustable resistor.

14. The device of claim 11 wherein the electrode-to-device includes a diode and the device-to-electrode path includes a diode.

15. The device of claim 14 wherein the diodes provide for bidirectional operation.

16. The device of claim 1 wherein the first anode electrode comprises a right ventricular electrode.

17. The device of claim 16 wherein the second anode electrode comprises a different right ventricular electrode.

18. The device of claim 16 wherein the second anode electrode comprises a case electrode.

19. The device of claim 16 wherein the cathode electrode comprises a left ventricular electrode.

20. The device of claim 1 further comprising a second resistance device coupled between another one of the anode terminal and the first anode electrode, the anode terminal and the second anode electrode and the cathode terminal and the cathode electrode.

21. The device of claim 20 further comprising a third resistance device coupled between another one of the anode terminal and the first anode electrode, the anode terminal and the second anode electrode and the cathode terminal and the cathode electrode.

22. The device of claim 1 further comprising an implantable lead for carrying one or more of the first and second anode electrodes and the cathode electrode and wherein the resistance device is included in the lead.

23. The device of claim 1 further comprising a case for housing the battery and wherein the resistance device is also housed in the case.

24. An implantable lead comprising:
an electrode;
a connector configured to connect to an implantable medical device;
a conductor defining a current path between the electrode and the connector and having a first end coupled to the electrode and a second end coupled to the connector; and
a first circuit defining a first path having a first resistance and a second circuit defining a second path having a second resistance, the first circuit and the second circuit arranged in parallel with respect to each other and disposed between the first end of the conductor and the second end of the conductor, the first circuit configured to block current from the connector to the electrode and to pass current from the electrode to the connector and, the second circuit configured to block current from the electrode to the connector and to pass current from the connector to the electrode.

25. The lead of claim 24 wherein the second circuit comprises a resistor.

26. The lead of claim 25 wherein the resistor comprises an adjustable resistor.

27. The lead of claim 26 wherein the adjustable resistor comprises a digitally programmable potentiometer.

28. The lead of claim 24 wherein the first circuit comprises a diode and the and the second circuit comprises a diode.

29. The lead of claim 28 wherein the diodes provide for bidirectional operation.

30. The lead of claim 24 wherein the first resistance and the second resistance are different.

* * * * *